US010980782B2

(12) United States Patent
Tang et al.

(10) Patent No.: US 10,980,782 B2
(45) Date of Patent: Apr. 20, 2021

(54) DE-EPOXIDIZED EPOTHILONE DERIVATIVE PREPARATION, PREPARATION OF SAME AND USE THEREOF IN THE TREATMENT OF TUMOR

(71) Applicants: Beijing Biostar Technologies Ltd., Beijing (CN); Chengdu Biostar Pharmaceuticals, Ltd., Sichuan (CN)

(72) Inventors: Li Tang, Beijing (CN); Rongguo Qiu, Beijing (CN)

(73) Assignees: BEIJING BIOSTAR TECHNOLOGIES, LTD., Beijing (CN); CHENGDU BIOSTAR PHARMACEUTICALS, LTD., Chengdu (CN)

( * ) Notice: Subject to any disclaimer, the term of this patent is extended or adjusted under 35 U.S.C. 154(b) by 0 days.

(21) Appl. No.: 16/075,904

(22) PCT Filed: Feb. 6, 2017

(86) PCT No.: PCT/CN2017/072971
§ 371 (c)(1),
(2) Date: Aug. 6, 2018

(87) PCT Pub. No.: WO2017/133706
PCT Pub. Date: Aug. 10, 2017

(65) Prior Publication Data
US 2019/0070152 A1 Mar. 7, 2019

(30) Foreign Application Priority Data
Feb. 6, 2016 (CN) .......................... 201610084006.0

(51) Int. Cl.
*A61K 31/427* (2006.01)
*A61K 47/40* (2006.01)
*A61K 47/44* (2017.01)
*A61K 47/34* (2017.01)
*A61P 35/00* (2006.01)
*A61K 9/00* (2006.01)
*A61K 31/7068* (2006.01)
*A61K 47/10* (2017.01)
*A61K 9/19* (2006.01)

(52) U.S. Cl.
CPC .......... *A61K 31/427* (2013.01); *A61K 9/0019* (2013.01); *A61K 31/7068* (2013.01); *A61K 47/10* (2013.01); *A61K 47/34* (2013.01); *A61K 47/40* (2013.01); *A61K 47/44* (2013.01); *A61P 35/00* (2018.01); *A61K 9/0053* (2013.01); *A61K 9/19* (2013.01)

(58) Field of Classification Search
CPC .. A61K 31/427; A61K 31/7068; A61K 47/10; A61K 47/34; A61K 47/40; A61K 47/44; A61K 9/0019; A61K 9/0053; A61K 9/19; A61P 35/00
See application file for complete search history.

(56) References Cited

U.S. PATENT DOCUMENTS

| | | | | |
|---|---|---|---|---|
| 6,670,384 B2 * | 12/2003 | Bandyopadhyay | .. | A61K 31/427 514/365 |
| 6,998,256 B2 * | 2/2006 | Arslanian | ............ | C07D 313/00 435/76 |
| 7,091,193 B2 * | 8/2006 | Sherrill | ..................... | A61K 9/19 514/365 |
| 7,323,573 B2 * | 1/2008 | Arslanian | ............ | C07D 313/00 548/204 |
| 8,618,085 B2 * | 12/2013 | Licari | .................. | A61K 9/0019 514/183 |
| 2004/0132692 A1 * | 7/2004 | Sherrill | ..................... | A61K 9/19 514/58 |
| 2005/0148543 A1 * | 7/2005 | Sherrill | ................ | A61K 9/0019 514/58 |
| 2005/0277682 A1 * | 12/2005 | Licari | .................. | A61K 9/0019 514/365 |

FOREIGN PATENT DOCUMENTS

| | | |
|---|---|---|
| CN | 1511192 | 7/2004 |
| CN | 1629283 A | 6/2005 |
| CN | 101112373 | 1/2008 |
| CN | 101137364 | 3/2008 |
| JP | 2004508810 A | 3/2004 |
| JP | 2006504745 A | 2/2006 |
| JP | 2007524655 A * | 8/2007 |
| JP | 2007530567 A | 11/2007 |

OTHER PUBLICATIONS

Vahdat (Semin Oncol 35, 2, S22-S30, 2008). (Year: 2008).*
Arslanian et al. (J Nat Prod 2002, 65, 570-572) (Year: 2002).*
Sausville et al., (Cancer Research, vol. 66, pp. 3351-3354) (Year: 2006).*
Johnson, British J of Cancer, 2001, 84(10), 1424-31). (Year: 2001).*
Gura (Science, v278, 1997, pp. 1041-1042) (Year: 1997).*
English translation of JP 2007524655 A (Year: 2007).*
Geyer et al. (The New England J of Medicine, 2006, p. 2733-43). (Year: 2006).*
Xeloda (https://www.breastcancer.org/research-news/xeloda-improves-survival-for-some, 2015). (Year: 2015).*

(Continued)

*Primary Examiner* — Umamaheswari Ramachandran
(74) *Attorney, Agent, or Firm* — Fox Rothschild LLP

(57) ABSTRACT

The present application discloses a pharmaceutical preparation comprising a de-epoxidized epothilone derivative, and especially relates to a preparation formulation of a compound with reduced allergens and toxicity; and also relates to the use thereof in the treatment of tumours, especially the use thereof in the treatment of solid tumours that are resistant to and fail to respond to other conventional chemotherapeutic agents, as well as the use thereof in the treatment of cancers alone or in combination with other tumour drugs or auxiliary drugs.

13 Claims, No Drawings

(56) References Cited

OTHER PUBLICATIONS

Wu, Qianhu, p. 349 from a book entitled "Clinical Medicine Handbook—Commonly Used Drugs for Treating Liver Disease," China Medicine Science and Technology Press, May 31, 2014.
Cortes et al., "Targeting the Microtubules in Breast Cancer Beyond Taxanes: The Epothilones," The Oncologist (2007); 12:271-280.
Thomas et al., "Ixabepilone Plus Capecitabine for Metastatic Breast Cancer Progressing After Anthracycline and Taxane Treatment," Journal of Clincial Oncology (2007); 25(33):5210-5217.

* cited by examiner

DE-EPOXIDIZED EPOTHILONE DERIVATIVE PREPARATION, PREPARATION OF SAME AND USE THEREOF IN THE TREATMENT OF TUMOR

TECHNICAL FIELD

The present application relates to a method for preparing a de-epoxidized epothilone derivative pharmaceutical formulation and a use thereof in a treatment of a cancer, particularly, to a method for preparing the pharmaceutical formulation of the compound, a clinical use of the compound, alone or in combination with other antitumor drugs, in a treatment of a cancer, especially an advanced breast cancer.

BACKGROUND

There are more than 14 million newly diagnosed cancer patients every year in the world, and cancer has become a common and frequently-occurring disease that is very harmful to humans. Since an early diagnosis and treatment of cancer has not yet reached a satisfactory level, most cancers will still relapse or metastasize to the whole body after a surgery or radiotherapy, and the cancer patients need to receive systemic treatment. At present, the main means for systemic therapy, especially for the treatment of patients with an advanced cancer, are still based on chemical drugs. For patients with an advanced breast cancer who have received treatments with high dosages of anthracycline ring antibiotics and taxanes, in addition to the approved capecitabine and gemcitabine, there are few drug options available for treatment. Furthermore, the effectiveness of gemcitabine used as a second- or third-line drug is unclear. Other drugs include vinorelbine, bevacizumab+paclitaxel, cisplatin, carboplatin, etoposide, vinblastine, and fluorouracil injections that are rarely used, however, there is little evidence indicating the drugs producing significant effects. Therefore, the development of safe and effective small molecule anticancer drugs is still a cancer treatment method and approach actively sought by multiple countries.

Epothilone A (EpoA) and epothilone B (EpoB) are novel compounds of 16-membered macrolide derived from polyketone, which are originally isolated from the soil bacterium Sorangium cellulosum strain So ce90. The structural formula is shown below. They are the epothilone firstly isolated, synthesized and confirmed (Hofle et al., 1996, Angew. Chem. Int. Ed. Engl. 35 (13/14): 1567-1569; Gerth et al., 1996. J. Antibiotics 49(6): 560-563). Polyketone compounds exist in nature in a variety of organisms and are synthesized by polyketone synthase PKS.

Epothilone has enormous potential for the treatment of cancers. Although not structurally similar, the action mechanism of epothilone is very similar to that of the chemotherapy drug paclitaxel, which induces tubulin polymerization and stabilizes microtubule assembly. These compounds exhibit potent cell killing power against different cancer cell lines. In particular, they have shown attractive effects on tumor cell lines with multidrug resistance (MDR), especially against taxanes-resistant tumor cell lines (Altmann et al., 2000. Biochem. Biophys. Acta. 1470(3): M79-91; Bollag et al., Cancer Res. 55(11): 2325-2333).

Although the epothilone compounds have significant therapeutic properties, it is still somewhat difficult for the skilled person to use them in pharmaceutical formulations and clinical applications due to certain properties. The compounds represented by Formula I in the present application can be safely formulated and can also be administered by injection. Many anticancer drugs have a toxicity-related effect, and due to toxicity, many effective anticancer drugs are limited to be used. Therefore, those skilled in the art are working on reducing or avoiding toxicity related to the anticancer drugs by appropriate formulation, administration or dosage to obtain an effective anticancer drug for clinical use.

SUMMARY

The present application relates to a pharmaceutical formulation and use thereof of a de-epoxidized epothilone administered parenterally for a treatment of tumors.

The formulation and method described in the present application relate to a formulation containing a de-epoxidized epothilone represented by Formula I, and a method for its preparation.

De-epoxidized epothilone derivatives have a very low solubility in an aqueous medium and will rapidly precipitate or degrade upon contacting with an aqueous medium, making it difficult to prepare a formulation. The pharmaceutical formulation of the present application solves this problem.

According to one aspect, the present application provides a pharmaceutical formulation containing a crystal of a compound represented by Formula I (de-epoxidized epothilone derivatives) and an excipient consisting of alcohols (such as ethanol) and at least one type of solubilizing agents (such as one to three types) miscible in a certain ratio, wherein the amount of alcohols (such as ethanol) is 20-50% (v/v) and the amount of each solubilizing agent can be 5-50% (v/v), respectively.

Formula I

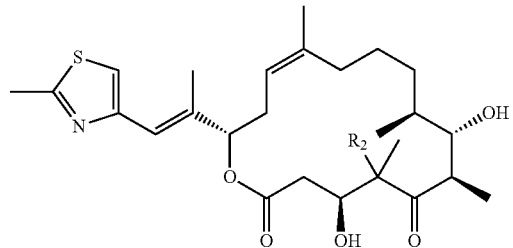

wherein in Formula I, $R_2$=$CH_3$ or H.

According to some embodiments of the present application, the solubilizing agent may be selected from the group consisting of: polyoxyethylenated castor oil (Cremorphore EL or Kolliphor® ELP), propylene glycol, PEG (such as polyethylene glycol 300-500), Solutol-HS15, Captisol and hydroxypropyl-β-cyclodextrin (HP-β-CD). When more than one solubilizer is used, each solubilizing agent may be present in an amount of from 5 to 50% (v/v).

According to some embodiments, the excipient preferably consists of absolute ethanol, polyoxyethylenated castor oil (Cremorphore EL or ELP) and propylene glycol. More preferably, the excipient has a composition of absolute ethanol:polyoxyethylenated castor oil:propylene glycol (v/v)=5:2:3.

According to some embodiments, the pharmaceutical formulation of the present application is in the form of a solution that can be administered parenterally.

According to some embodiments, the compound contained in the pharmaceutical formulation of the present application is the compound wherein $R_2$=$CH_3$ in Formula I.

According to some embodiments, the concentration of the compound of Formula I in the pharmaceutical formulation of the present application is 5-20 mg/ml, preferably 10 mg/ml. The pharmaceutical formulation can be contained in a separate glass vial of 3 ml or 5 ml.

According to another aspect of the present application, the present application relates to a use of the above pharmaceutical formulation for the preparation of an antitumor drug.

According to still another aspect of the present application, the present application provides a method for treating a tumor in a patient, the method includes administering the pharmaceutical formulation of the present application to the patient.

According to still another aspect of the present application, the present application provides the above pharmaceutical formulation for use in an antitumor treatment or treating a tumor patient.

According to some embodiments of the present application, the antitumor drug is an antitumor drug against a solid tumor. Specifically, the solid tumor may be selected from the group consisting of breast cancer, lung tumor, lymphoma, colon cancer, prostate cancer, nervous system tumor (brain cancer), ovarian cancer, liver cancer, head and neck tumor, stomach cancer and kidney cancer. Preferably, the tumor is breast cancer, lung cancer, liver cancer, colorectal cancer and stomach cancer.

According to some embodiments of the present application, the antitumor drug is used for treating a patient who has not been previously treated for a solid tumor or has been treated for a solid tumor.

According to some embodiments of the present application, the antitumor drug is used for treating a tumor that is ineffective or relapsed with a taxane antitumor drug treatment or a tumor that is difficult to treat.

According to some embodiments of the present application, the pharmaceutical formulation of the present application is diluted with a certain amount of suitable parenteral diluent such that the concentration of said derivatives is from 0.05 mg/ml to 0.5 mg/ml. The diluent can be used is 5% glucose injection, sodium lactate Ringer's injection, sterile water for injection or sterile physiological saline for injection, for example, sterile physiological saline for injection.

According to some embodiments, the solubilizing agent contained in the pharmaceutical formulation of the present application is Captisol (β-cyclodextrinsulfobutyl ether), to form a 5-20%, preferably a 8% Captisol solution (with or without ethanol and propylene glycol) as a pharmaceutical formulation. The Captisol-containing pharmaceutical formulation can be diluted with a buffer solution to form a diluted pharmaceutical formulation containing 0.5 mg/ml to 1.0 mg/ml of the compound of Formula I for clinical use. The buffer solution can be, for example, a phosphate buffer. Alternatively, the Captisol formulation can be lyophilized. When using, a suitable common diluent (with or without ethanol and propylene glycol) in certain amount is used for reconstitution such that the final concentration of the compound of Formula I is from 0.5 mg/ml to 1.0 mg/ml.

According to one aspect of the present application, the method for treating a patient with an antitumor drug includes administering to the patient a therapeutically effective amount of a compound of Formula I, intravenously or orally. For intravenous or oral administration, or both of intravenous and oral administration, an example of a dosage for a human is 10 mg/m$^2$/day to 175 mg/m$^2$/day, which may be administered in a single dose or multiple doses. According to some embodiments of the present application, the pharmaceutical formulation is administered intravenously. For example, intravenous administration is performed as an intravenous infusion from day 1 to day 5 once a day for 5 consecutive days and every 3 weeks as one treatment course. The compound of Formula I is administered intravenously at a dosage of from about 10 mg/m$^2$/day to 50 mg/m$^2$/day, for example, about 40 mg/m$^2$/day.

When administered orally, the compound of Formula I is preferably used together with a pharmaceutically acceptable acid neutralizing buffer, such as a carbonate or phosphate. A solution of Formula I contains a phosphate buffer (pH is about 8, concentration is 1 M), and the buffer can neutralize the acid in the patient's stomach to reduce the rate of degradation of the compound of Formula I. Oral administration can be carried out in a solid oral dosage form (such as a tablet or powder, an enteric coated pill or capsule) or a liquid oral dosage form.

According to some embodiments of the present application, the compound of Formula I is administered intravenously over a period of from about 30 minutes to about 3 hours, such as within about 1.5 hours.

According to some embodiments of the present application, the pharmaceutical formulation can be used in combination with at least one of other anticancer drugs.

According to some embodiments of the present application, the other anticancer drugs are selected from the group consisting of chemotherapeutic drugs 5-fluorouracils such as capecitabine and Gemcitabine, an alkylating agent such as Carboplatin and Cisplatin, targeted drugs such as Iressa, Gleevec, Kemena, Lapatinib, monoclonal antibody drugs such as trastuzumab (Herceptin, Trastuzumab), bevacizumab (Avastin, Bevacizumab), Pertuzumab (Perjeta, Pertuzumab), tumor immunotherapeutic drugs of anti-PD-1/PD-L1 and anti-CTLA-4, and hormone endocrine therapy drugs, such as Norred and Letrozole.

According to some embodiments of the present application, the compound is administered for one treatment course of every 3 weeks, wherein the compound of Formula I is administered by an intravenous infusion from day 1 to day 5, once a day, for 5 consecutive days. When the compound of Formula I is used in combination with capecitabine, capecitabine is administered orally from day 1 to day 14, twice a day, for 14 consecutive days. For example, the compound of Formula I is administered intravenously at a dosage of from about 10 mg/m$^2$/day to 50 mg/m$^2$/day; and capecitabine is administered orally at a dosage of from about 1000 mg/m$^2$/day to 2500 mg/m$^2$/day. As another example, the compound of Formula I is administered intravenously at a dosage of about 30 mg/m$^2$/day, and capecitabine is administered orally at a dosage of about 2000 mg/m$^2$/day.

The present application also relates to a method for treating a tumor, the method includes administering a compound of Formula I to a patient in need thereof.

The present application also relates to a method for preparing a crystal of a compound of Formula I, the method includes steps of: crystallizing the compound of Formula I by adding the compound of Formula I into an alcohol (such as ethanol), then mixing with water in a ratio of alcohol to water of 40% to 60% v/v, preferably 50% v/v (The amount of mixture of alcohol and water with respect to the compound is 20-50 mL/g.), precipitating a crystal of the compound of Formula I at a temperature lower than the room temperature, vacuum drying or lyophilization the crystal for 24 hours to 98 hours, preferably 48 hours to obtain the crystal of the compound.

The pharmaceutical formulation of the present application is unique and stable well. The clinical drug administration of the formulation is effective, which fully exhibits the therapeutic effects of the de-epoxidized epothilone derivative and the advantages thereof with low adverse effects, especially having substantially no bone marrow suppression toxicity.

DETAILED DESCRIPTION OF THE INVENTION

The pharmaceutical formulation of the present application can be obtained by the following method. The compound of Formula I is crystallized by using an alcohol such as ethanol and water at a ratio of alcohol to water of 40% to 60% v/v, preferably 50%, in an amount of 20 to 50 mL/g. The crystal obtained are vacuum dried or lyophilized for 24 hours to 98 hours, preferably 48 hours to obtain a crystal of the compound for storage or for preparing the formulation. Residual solvent and water are preferably removed from the crystal to reduce harmful toxicity to humans. In order to minimize the amount of polyoxyethylenated castor oil in the formulation, the formulation is prepared from the dried compound of Formula I and a mixture containing 50% v/v absolute ethanol (USP), 30% v/v propylene glycol (USP) and 20% v/v other solubilizing agents as an excipient. The other solubilizing agents are preferably polyoxyethylenated castor oil (Cremophor EL or ELP). A sufficient amount of excipients are provided to form a solution containing a compound of Formula I at a concentration of about 5 mg/ml to about 20 mg/ml, preferably about 10 mg/ml, which may make the initial formulation and the diluted clinically compatible formulation of the compound of Formula I have a better stability. Meanwhile, the addition of propylene glycol reduces the concentration of castor oil to a minimum required amount, thereby reducing the allergic reaction induced by the solvent. The level of allergic reaction observed with the formulation of the present application is significantly lower than some other antitumor formulations (containing 50% castor oil).

The compound of Formula I in the pharmaceutical formulation provided by the present application may exist in a form of various optical isomers or stereoisomers, or a salt formed with various organic and inorganic acids.

The formulation prepared by the present application can be sterile filled into a glass tube or a vial, preferably a 5 ml vial, containing about 0.5 ml to about 5 ml of the formulation. A capped drug sealed by a butyl rubber plug coated with a polytetrafluoroethylene film can be stored for at least 24 months at a temperature of at least 2-8° C.

For clinical use, the compound in the formulation of the present application can be diluted with a suitable diluent, such as 5% glucose injection, sterile water for injection, sterile physiological saline for injection or lactate Ringer's injection. The volume of the diluted injection is from about 50 ml to about 300 ml, preferably from about 100 ml to about 250 ml. Prior to administration, the diluted solution can be stored at room temperature for no less than about 24 hours such that the final administration concentration of the compound of Formula I is preferably from about 0.05 mg/ml to 0.5 mg/ml.

The compound of Formula I can be administered with one or more other substances, such as antiemetics or H1 or H2 antihistamines, to prevent nausea, allergies or gastrointestinal reactions.

The formulation prepared by the present application can be used for intravenous infusion after being diluted by the above method, the intravenous infusion time is 30 minutes to 3 hours, preferably 1.5 hours, and the intravenous infusion is carried out once a day and for 5 consecutive days. Every 21 days is one treatment course. The formulation prepared by the present application can be combined with oral administration of capecitabine of 1000 mg/m$^2$/time, which is administered twice a day for 1 to 14 days, and every 21 days is one treatment course. The compound of Formula I is administered in one treatment course of every 3 weeks, from day 1 to day 5, the compound is administered once a day by intravenous infusion and for 5 consecutive days. The intravenous infusion is carried out in a period of from about 45 minutes to about 3 hours, preferably in a period of about 1.5 hours.

Other useful solubilizing agents are PEG, Captisol and Solutol-HS 15, which can also be used in admixture with ethanol and/or propylene glycol.

The present application also relates to a method for treating a cancer in a patient, the method includes administering to the patient one or more compounds of Formula I or formulations thereof in a therapeutically effective amount, wherein the compound of Formula I or formulation thereof are administered preferably by intravenous infusion. In some embodiments, a dosing regimen and dosage for the de-epoxidized epothilone of Formula I is described, which is administered in a form of individual doses. Depending on many factors such as the metabolism of the drug, the general condition of the patient, the severity of the cancer disease and the difference in the adverse reactions to the drugs, for a particular patient, the dosage and the frequency of administration is variable. Preferably, the pharmaceutical formulation of the present application is administered once a day for 5 consecutive days, and every about 3-4 weeks (18-28 days, preferably 3 weeks, 18-24 days) is one treatment course. For each treatment course, the pharmaceutical dosage administered by intravenous infusion is from about 5 mg/m$^2$/day to 50 mg/m$^2$/day, and more preferably from 20 mg/m$^2$/day to 40 mg/m$^2$/day. Generally, if the patient has a drug-related adverse reaction, the administration is terminated or the dose is lowered, or the administration is delayed. When the administration is carried out by a reduced dose, the reduced dose is 20%-30%, preferably 20% of the initial dose.

The present application further provides a use of a de-epoxidized epothilone derivative of Formula I for antitumor. During treating cancers, patients are administered parenterally with the pharmaceutical formulation of the present application in a therapeutically effective amount. If necessary, the administration can be repeated to prevent the spread of cancer or to cure cancer. On the other hand, the pharmaceutical formulation of the present application may be used alone or in combination with other anticancer drugs or therapies. Other anticancer drugs can be selected from the group consisting of antimetabolites such as 5-fluorouracil and Gemcitabine, an alkylating agent such as Carboplatin and Cisplatin, targeted drugs such as Iressa, Gleevec, Kemena, Lapatinib, monoclonal antibody drugs such as trastuzumab (Herceptin, Trastuzumab), bevacizumab (Avastin, Bevacizumab), Pertuzumab (Perjeta, Pertuzumab), tumor immunotherapeutic drugs of anti-PD-1/PD-L1 and anti-CTLA-4, and hormone endocrine therapy drugs, such as Norred and Letrozole. The combination may be administered in a sequential manner, that is, the pharmaceutical formulation of the present application and other anticancer drugs may be administered successively, or may be administered simultaneously.

The pharmaceutical formulations of the present application are useful for the treatment and/or prevention of metastatic tumors as well as primary tumors. The present application also includes treatments of patients who have previously received radiotherapy and chemotherapy for solid tumors, either alone or simultaneously, as well as treatments of tumors that are naturally insensitive to, or later become insensitive to, the taxane.

In some embodiments, the pharmaceutical formulation of the present application is administered intravenously once a day for 5 consecutive days with every about 3 weeks as one treatment course, and the dosage for a daily intravenous infusion is about 5 mg/m$^2$/day to 50 mg/m$^2$/day, and more preferably 20 mg/m$^2$/day to 40 mg/m$^2$/day.

The compound of Formula I of the present application can be administered in combination with other anticancer drugs, including alkylating agents, antimetabolites, antibiotics, hormones, plant products, monoclonal antibody drugs or tumor immunotherapeutic drugs.

The present application also includes a use of a pharmaceutical formulation containing a compound of Formula I, alone or in combination with capecitabine, for the treatment of an advanced breast cancer, particularly human epidermal growth factor receptor 2-(HER2) negative breast cancer, preferably a HER2 negative and hormone receptor positive (Hormone receptor (ER or/and PR)-positive) breast cancer.

The present application also provides a use of a compound of Formula I (or called "de-epoxidized epothilone derivative") in combination with an immunotherapeutic drug for the treatment of a solid tumor including an advanced breast cancer or lung cancer.

The present application provides a method of treating a tumor patient, the method includes administering parenterally or orally the pharmaceutical formulation described herein to a patient.

According to some embodiments, the pharmaceutical formulation is administered in a treatment course of 21 days or more than 21 days, intravenously or orally, and may be administered in a single dose or in multiple doses in one course. Multiple doses are preferred.

When a de-epoxidized epothilone derivative of the present application is used in combination with capecitabine for the treatment of an advanced metastatic breast cancer, a therapeutically effective amount of a de-epoxidized epothilone derivative is used in combination with a certain dose (2000-2500 mg/m$^2$/day) of capecitabine.

DETAILED DESCRIPTION

The following examples are for illustrative purposes only and are not to be construed as limiting the application.

PREPARATION EXAMPLES

Example 1. Preparation of the Formulation

The method for preparing the formulation includes: preparation of crystals, formulating, filtration, filling, capping, sealing, etc. of the formulations.

1) 75 g dried compound of Formula I (where R$_2$=CH$_3$) was dissolved in 100% ethanol to a concentration of 20 mL/g, and then sterile filtered by using a 0.2 μm membrane, and the filtrate was slowly added with 40% water while stirring, then a small amount of crystal seeds was added, after that stirring continued for 30 minutes. The remaining water was then added to the solution such that an ethanol concentration was 50%. During stirring, the temperature of the solution containing crystals was brought to 4° C. by using a cooling water bath, and stirring was continued for 2 to 12 hours. The crystals were vacuum filtered, followed by rapid washing with a cooled 30% aqueous ethanol solution at 4° C. The crystals were dried in a vacuum oven for 48 hours to obtain 60 g products, which were stored in a clean and dry glass bottle.

2) The product obtained in step 1) was dissolved in absolute ethanol (Pharmacopoeia grade) in an amount of 20 g absolute ethanol/g product to form a solution, and under stirring, 21.0 g polyoxyethylenated castor oil (Pharmacopoeia grade) was added, and the mixture was stirred and mixed for 15 minutes. Then, 31.1 g propylene glycol (Pharmacopoeia grade) was added to the mixed solution and stirring was continued for 10-15 minutes. Finally, 19.45 g absolute ethanol (Pharmacopoeia grade) was added, and stirring was continued until the solution was clear (5-10 minutes) to obtain a formulation solution containing the compound of Formula I in a concentration of 10 mg/mL, wherein the volume ratio of anhydrous ethanol:polyoxyethylenated castor oil:propylene glycol is 5:2:3.

3) The formulation obtained in step 2) was sterilized by filtration through a 0.2 μm filter (Millipore), and then filled into a 5 ml vial after sterilizing. Each vial was filled with 3 ml+0.25 ml or 5 ml+0.3 ml. After that, the vial was capped and sealed, and stored at 2 to 8° C. for use. The storage time was longer than 24 months. No degradation or precipitation was observed during the storage. The formulation has good solubility and is stable, which is good for storage.

4) The pharmaceutical formulation was diluted by physiological saline in a ratio of 1:20 or 1:50. The color, the appearance, pH value, visible foreign substance, materials contained in the pharmaceutical formulation and the contents thereof did not change significantly within 24 hours at room temperature, indicating that the compound of Formula I can be diluted with common solutions without incompatibility. The pharmaceutical formulation was stable for at least 24 hours when stored at room temperature.

Example 2: Preparation of the Formulation

The primary objective of this example is to increase the solubility of the compound of Formula I by the addition of Captisol, with reduced amount of polyoxyethylenated castor oil or without it, so as to reduce the hypersensitization adverse effects of patients.

1. 100 g Captisol was dissolved in 200 ml water (WFI) to obtain a Captisol solution having a concentration of 50% Captisol;

2. 400 mg compound of Formula 1 was dissolved in 10 ml ethanol to obtain an ethanol solution of the compound having a concentration of 40 mg/ml.

3. Prepare a solution of the compound containing Captisol according to the following table:

|  | Formulation A | Formulation B | Formulation C |
| --- | --- | --- | --- |
| Captisol solution (1) | 5 ml | 2.0 ml | 2.0 ml |
| Compound of Formula I |  | 5 mg | 5 mg |

-continued

|  | Formulation A | Formulation B | Formulation C |
|---|---|---|---|
| Ethanol solution of the compound (2) | 2.5 ml | | |
| Water | 2.5 ml | 3.0 ml | 8 ml |
| Composition of the formulation | 25% Captisol: 25% Ethanol 10 mg/ml (compound in solution) | 20% Captisol 1 mg/ml (compound in solution) | 10% Captisol 0.5 mg/ml (compound in solution) |
| Recovery rate by HPLC (24 h) | 98.6% | 98.9% | 98.2% |

4. Formulations A, B, and C were completely dissolved and clear after preparation. After being placed at room temperature for 0 h and 24 h, 1 ml was sampled respectively. After centrifugation at 12,000 rpm for 10 minutes, the supernatant was taken, diluted with acetonitrile solvent, and analyzed by HPLC. The recovery rate was >98%.

5. After stored for 24 hours at room temperature, the compound of Formula I was completely dissolved in Formulation A, B and C and no precipitation occurred within 24 hours, indicating that the drug has a good solubility and is stable, which is good for storage. After diluting formulation A, the concentration of Captisol was 2.5% or 1.25%, and no precipitation occurred within 24 hours.

6. Formulation A was prepared as a concentrated solution of 5 ml for storage. In clinical use, a diluent such as sterile water for injection, sterile physiological saline for injection or phosphate buffer was used to prepare a solution containing 0.5 mg/ml to 1.0 mg/ml of the compound of Formula 1. The diluted solution had no significant changes within 12 hours at room temperature.

7. 10 ml of Formulation B was lyophilized for 48 hours to form a white powder. No degradation of the sample was detected by HPLC analysis, indicating that the lyophilized has a good stability and is good for storage.

8. The dried sample in step 7 was added with 10 ml or 20 ml diluent such as sterile water for injection, sterile physiological saline or phosphate buffer (with or without 1% propylene glycol and 10% ethanol) to prepare a solution containing 0.5 mg/ml to 1.0 mg/ml of the compound of Formula 1. The diluted solution had no significant changes within 12 hours at room temperature.

Biological Activity Experiments

The pharmaceutical formulations of the present application used in the following biological activity experiments were formulations prepared in Example 1.

Example 3. Bioavailability of Oral Administration

The pharmaceutical formulation containing the compound of Formula I (volume ratio of anhydrous ethanol: polyoxyethylenated castor oil:propylene glycol is 5:2:3) was diluted with phosphate buffer to form a solution containing 1.0 mg/ml of the compound of Formula I. The obtained solution was administered to Beagle dog by intravenous infusion (for 1 hour) or fed through oral tube, respectively. Then blood samples were collected at different times (from the start of the administration to 24 hours), the blood concentrations were determined, and the AUC and bioavailability of the formulation in the blood of the Beagle dog were calculated.

| Dosage (mg/kg) | Beagle dog ID = 201 | Beagle dog ID = 202 | Bioavailability |
|---|---|---|---|
| 3.6 (mg/kg) blood concentration (ng/mL$^{-1}$) | AUC (intravenous infusion) 16258 | AUC (oral administration) 9232 | F (%) 56.8 |

This example demonstrates that the compounds of Formula I (especially R=CH$_3$) have good bioavailability (>50%) when administering to Beagle dogs orally, which can be used in the preparation of oral formulations.

Example 4

Antitumor experiments of the pharmaceutical formulation of the present application administered by intravenous injection in vivo against a human tumor cell xenograft model.

1) Number of animals: there are 6 nude mice for each experimental group and positive control group; weighing: 20-21 g. The negative control has two groups.

2) Dosage and regimen of administration: the dose is described in the portion of the experimental results. The injection volume is 0.2 ml/mouse.

3) Control groups: the negative control is the corresponding vehicle. The positive control is taxol which is a widely clinically used antitumor drug.

4) Main Steps of the Experiment:

Under aseptic conditions, a tumor source with vigorous growth was taken to prepare a cell suspension of about 1-3×10$^7$/ml by a homogenization method. The suspension was injected subcutaneously into subaxillary region of nude mice at 0.2 ml/mouse. The drug was administered upon the tumor touchable. The drug was administered according to the regime. The animals in each group were sacrificed after the administration of three to four weeks. The tumors were taken and weighed, and the tumor inhibition rate was calculated according to the following formula:

Tumor inhibition rate %=[(average tumor weight of the negative control group−average tumor weight of the compound administered group)/average tumor weight of the negative control group]×100%

5) Experimental Results:

The formulation of the present application was administered at 2.5, 1.0, 0.4 mg/kg/d, iv×10 bid, and the tumor inhibition rate against a solid tumor model having human colorectal cancer HCT-15 subcutaneously xenografted into subaxillary region was 87.74%, 77.42% and 60.19%, respectively. In the control group of taxol, the drug was administered at 10 mg/kg/time, iv×7qd, and the tumor inhibition rate was 52.2%.

The compound of Formula I was administered as the formulation of the present application at 2.5, 1.0, 0.4 mg/kg/time, iv×10 bid, and the tumor inhibition rate against a solid tumor model having human liver cancer Hep-G2 subcutaneously xenografted into subaxillary region was 81.26%, 69.41% and 58.67%, respectively. In the control group of taxol, the drug was administered at 10 mg/kg/time, iv×7qd, and the tumor inhibition rate was 52.2%.

The compound of Formula I was administered as the formulation of the present application at 2.5, 1.0, 0.4 mg/kg/time, iv×10 bid, and the tumor inhibition rate against a solid tumor model having human prostate cancer PC-3 subcutaneously xenografted into subaxillary region was 70.00%, 61.15% and 49.08%, respectively. In the control group of taxol, the drug was administered at 10 mg/kg/time, iv×7qd, and the tumor inhibition rate was 41.31%.

This example fully demonstrates that the compound of Formula I can be used for the preparation of a medicament for treating solid tumors such as colorectal cancer, liver cancer, prostate cancer, etc., and the therapeutic effect is superior to that of the control group.

Example 5

Therapeutic effect of the compound of Formula I in combination with other chemotherapeutic drugs on a solid tumor model having human tumor colorectal cancer subcutaneously xenografted into subaxillary region The compound of Formula I was administered at 0.4 mg/kg/d, iv×10 bid, or the compound of Formula I at the above dosage was administered in combination with Gemcitabine at ED50 dosage 50 mg/kg/d, iv×3, q3d, or Gemcitabine was administered alone at 50 mg/kg/d, iv×3, q3d. The tumor inhibition rate against a solid tumor model having human lung cancer A549 subcutaneously xenografted into subaxillary region was 51.28%, 82.18% and 39.23%, respectively.

The compound of Formula I was administered at 0.4 mg/kg/d, iv×10 bid, or the compound of Formula I at the above dosage was administered in combination with Cisplatin (DDP) at ED50 dosage 1 mg/kg/d, iv×7, qd, or DDP was administered alone at 1 mg/kg/d, iv×7, qd. The tumor inhibition rate against a solid tumor model having human liver cancer Hep-G2 subcutaneously xenografted into subaxillary region was 58.67%, 85.33% and 45.33%, respectively.

The compound of Formula I was administered at 0.4 iv×10 bid, or the compound of Formula I at the above dosage was administered in combination with 5Fu at ED50 dosage 15 mg/kg/d, iv×7, qd, or 5 Fu was administered alone at 15 mg/kg/d, iv×7, qd. The tumor inhibition rate against a solid tumor model having human colorectal cancer HCT-15 subcutaneously xenografted into subaxillary region was 60.19%, 73.68% and 42.71%, respectively.

A combination of the compound of Formula I at a low dose in vivo with several commonly used antitumor chemotherapeutic drugs (at ED50 dosage) shows a synergistic or enhanced effect: a combination with Gemcitabine shows a synergistic effect on lung cancer A549, a combination with DDP shows a synergistic effect on liver cancer HepG2 and a combination with 5Fu shows a synergistic trend on colorectal cancer HCT-15.

Example 6. Intravenous Administration of the Compound

Compound of Formula I was evaluated in terms of MTD (maximum tolerated dose), DLT (dose limiting toxicity), pharmacokinetics and pharmacodynamics by subjecting 21 patients with metastatic advanced solid tumors who met the inclusion criteria to the treatments with the compound at six dosages (25-225 mg/m$^2$).

There are 5 male patients and 16 female patients, aged 25-64 years, including 10 patients with breast cancer, 4 patients with non-small cell lung cancer, 2 patients with malignant melanoma, 1 patient with sigmoid colon cancer, 1 patient with submandibular adenocarcinoma, 1 patient with scapular small cell malignant tumor and 1 patient with cystosarcoma phylloides, and 19 of whom had previously been treated with other chemotherapy drugs.

The formulation of the compound of Formula I, prepared according to Example 1, was stored in a small vial with the amount of 50 mg: 5 ml. An appropriate amount of the formulation was taken according to the surface area of patients, diluted with 100 ml physiological saline for injection, and intravenous infused by a quantitative infusion pump with a constant speed over 3 hours. It was administered once every three weeks on the first day, and three weeks was a treatment course. Patients were monitored for DLT during the treatment. The results indicate that the compound of Formula I can be administered every 3 weeks at dosage up to 170 mg/m$^2$ without severe toxicity or allergies.

In the second study, 15 patients with advanced solid tumors who met the inclusion criteria received treatments at three dosages (35, 40, 45 mg/m$^2$/d) of the compound of Formula I. There were 3 male and 12 female in the patients. Among them, 8 patients were breast cancer patients, two were rectal cancer patients, and one had non-small cell lung cancer, one had stomach cancer and one had left scapular malignant tumor. All patients had previously been treated with other chemotherapy drugs. Intravenous infusion was used over 1.5 hours per day, continuous infusions for 5 days, every 3 weeks as 1 treatment course. The results indicate that the compound of Formula I can be administered daily at a dosage up to 40 mg/m$^2$/day (MTD) for 5 consecutive days, every 3 weeks as one treatment course. Treatment for at least 6 treatment courses did not lead to serious toxicity showing the compound safe and controllable. In particular, there were no severe adverse effects of myelosuppression that would be occurred to other conventional chemotherapeutic drugs or other administration modes. Among the subjects, 13 patients completed the efficacy evaluation of more than two treatment courses, of which the best efficacy for three patients (3 PR), 3 patients as PD, and 7 patients as SD, and thus the efficacy of the compound was definite. This study further demonstrates that, patients with breast cancer, rectal cancer, lung cancer, etc., who had previously been treated with chemotherapy drugs, indeed have response to the treatment of the compound of Formula I.

Example 7. Intravenous Administration of the Compound of Formula I in Combination with Capecitabine for Patients with Advanced Breast Cancer 33 patients with metastatic breast cancer (aged 28-71 years) who met the inclusion criteria received treatments at three dosages (25, 30, 35 mg/m$^2$/d) of the compound of Formula I. The compound was administered intravenously for 1.5 hours per day for a consecutive 1-5 days, which combined with capecitabine (2000 mg/m$^2$/d, twice a day, for consecutive 14 days), 3 weeks as one treatment course. All patients had previously been treated with other chemotherapeutic drugs, wherein 30 patients had previously received treatments with chemotherapy for treating metastatic cancers, 27 patients had previously received treatments of taxane and anthracycline for metastatic cancers, and 11 patients had received treatments with more than 3 types of drugs including taxane, anthracycline and capecitabine. The results indicate that, 32 patients were evaluated for efficacy, including 1 patient as CR, 13 patients as PR, 15 patients as SD, and 3 patients as PD. The objective remission rate (ORR) (complete remission CR and partial remission PR) is 43.8%. The median time to remission is 6 weeks. The median number of treatment course is 6 (it is the treatment course number that is required by the protocol to stop the trial). The median remission duration is 7.8 months. The median PFS is 7.9 months. During the treatment period, no patients died and no SAE, numbness of the hands and feet (PN) and swelling and pains of the hands and feet (hand and foot syndrome), such common adverse effects occurred, and no severe adverse effects of myelosuppression occurred. A combination of compound in the present application with capecitabine does not increase the toxicity and side effects of capecitabine, especially hand and foot syndrome. It is thus demonstrated that the formulation containing the compound of Formula I of the present application and the regimen of administration thereof have significant efficacy with low and controllable toxicity.

We claim:

1. A method for treating a tumor in a patient, comprising administering to a patient in need thereof a pharmaceutical formulation, the pharmaceutical formulation comprising a crystal of a compound represented by Formula I and an excipient consisting of ethanol and at least one solubilizing agent, wherein said ethanol is miscible with the solubilizing agent and in the amount of 20-50% (v/v) of the total volume of said excipient,

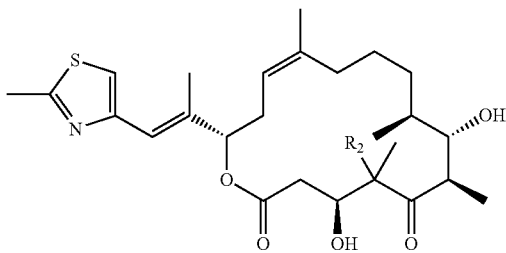

Formula I wherein in Formula I, $R_2$=CH3 or H,
wherein the compound is administered to the patient at a dosage of from about 30 mg/m$^2$/day to about 40 mg/m$^2$/day by intravenous infusion over a period of about 1.5 hours for first 5 consecutive days every three weeks, or is administered orally to the patient at a dosage of from about 100 mg/m$^2$/day to 150 mg/m$^2$/day from once to thrice per day for first 5 consecutive days every three weeks, and
wherein the tumor is selected from the group consisting of breast cancer and lung cancer.

2. The method according to claim 1, wherein the compound is administered to the patient at a dosage of from about 30 mg/m$^2$/day to about 35 mg/m$^2$/day.

3. The method according to claim 1, wherein the tumor is a solid tumor.

4. The method according to claim 1, wherein the pharmaceutical formulation is used for treating a tumor that is effective with a treatment of a microtubule stabilizer.

5. The method according to claim 1, wherein the tumor has not been previously treated or has been treated.

6. The method according to claim 1, wherein the compound is administered for one treatment cycle of every 18-24 days; wherein from day 1 to day 5, the compound is administered by intravenous infusion once daily for consecutive 5 days.

7. The method according to claim 1, wherein the pharmaceutical formulation is used in combination with a second anti-cancer drug that is capecitabine, Gemcitabine.

8. The method according to claim 7, wherein when used in combination with capecitabine, the compound of Formula I is administered for one treatment cycle of every three weeks, wherein from day 1 to day 5, the compound is administered by intravenous infusion once daily for 5 consecutive days; and capecitabine is administered orally twice daily for 14 consecutive days from day 1 to day 14.

9. The method according to claim 8, wherein capecitabine is administered orally at a dosage of from about 1000 mg/m$^2$/day to about 2500 mg/m$^2$/day.

10. The method according to claim 1, wherein when used alone, the compound of Formula I is administered intravenously at an initial dosage of about 40 mg/m$^2$/day; or when used in combination with capecitabine, the compound of Formula I is administered intravenously at an initial dosage of about 30 mg/m$^2$/day and capecitabine is administered orally at a dosage of about 2000 mg/m$^2$/day.

11. The method according to claim 5, wherein the tumor is a human epithelial growth factor receptor 2 (HER2) negative breast cancer.

12. The method according to claim 11, wherein the tumor is a HER2 negative and hormone receptor-positive breast cancer.

13. A method for treating an advanced non-small cell lung cancer (NSCLC) in a patient that has not been previously treated or has been treated, comprising administering to the patient a pharmaceutical formulation, the pharmaceutical formulation comprising a crystal of a compound represented by Formula I and an excipient consisting of ethanol and at least one solubilizing agent, wherein said ethanol is miscible with the solubilizing agent and in the amount of 20-50% (v/v) of the total volume of said excipient,

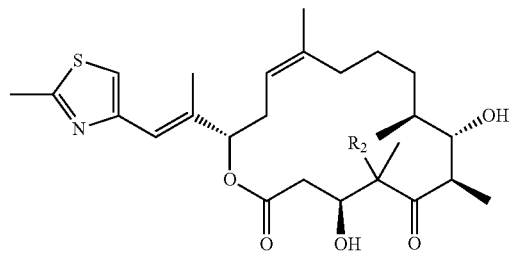

Formula I wherein in Formula I, $R_2$=CH3 or H, and
wherein the compound is administered to the patient at a dosage of from about 30 mg/m$^2$/day to about 40 mg/m$^2$/day by intravenous infusion over a period of about 1.5 hours, for first 5 consecutive days every three weeks, or is administered orally to the patient at a dosage of from about 100 mg/m$^2$/day to 150 mg/m$^2$/day from once to thrice per day for first 5 consecutive days every three weeks.

\* \* \* \* \*